United States Patent [19]
Lofgren et al.

[11] 3,989,040
[45] Nov. 2, 1976

[54] PATIENT EXTREMITY SURGICAL DRAPE
[75] Inventors: Lewis C. Lofgren, Appleton, Wis.;
Stephen E. Farrow, Concord, Calif.
[73] Assignee: Kimberly-Clark Corporation,
Neenah, Wis.
[22] Filed: Dec. 18, 1975
[21] Appl. No.: 642,030

Related U.S. Application Data
[63] Continuation of Ser. No. 558,650, March 17, 1975, abandoned.

[52] U.S. Cl. ............................................ 128/132 D
[51] Int. Cl.$^2$ .................................... A61F 13/00
[58] Field of Search ............ 128/132 R, 132 D, 292, 128/165

[56] References Cited
UNITED STATES PATENTS

| | | | |
|---|---|---|---|
| 3,030,957 | 4/1962 | Melges | 128/292 |
| 3,037,507 | 6/1962 | Melges | 128/132 D |
| 3,335,719 | 8/1967 | Boucher | 128/132 D |
| 3,424,153 | 1/1969 | Lewis | 128/132 D |
| 3,878,843 | 4/1975 | Morgan | 128/132 D |

*Primary Examiner*—Lawrence W. Trapp
*Attorney, Agent, or Firm*—Daniel J. Hanlon, Jr.; William D. Herrick; Raymond J. Miller

[57] ABSTRACT

An improved surgical drape adapted to cover a patient extremity such as an arm or a leg during a surgical procedure. The drape is tubular in construction having one end closed and means for adhesively attaching it to the patient along a slit adjacent to the open end. For disposability it is fabricated from a nonwoven fabric on the surface contacting the patient and, bonded thereto, a liquid-proof film forming the outside surface. Preferred embodiments are described wherein the drape is formed from a flat sheet and has a reinforced side seam and end. A preferred method of telescope folding the drape for improved safety and speed of applicaton is also disclosed.

7 Claims, 11 Drawing Figures

PATIENT EXTREMITY SURGICAL DRAPE

This is a continuation of application Ser. No. 558,650, filed Mar. 17, 1975, and now abandoned.

BACKGROUND OF THE INVENTION

1. Field of the Invention

The present invention relates to surgical drapes adapted to cover a patient extremity during the operative procedure. In most, if not all, surgical procedures it is necessary to isolate the area of the incision from surrounding areas in order to reduce the risk of contamination and infection. In more complicated cases, such as hip surgery, this necessitates covering essentially the entire patient outside of the operative site, including extremities such as arms and legs. Surgical drapes for these uses are normally sterilized prior to use and folded for compact packaging and storage.

2. Description of the Prior Art

Historically, when surgery has necessitated draping of a patient's extremity such as an arm or a leg, it has been simply covered with a muslin sheet. Particularly in surgical procedures which necessitate moving the extremity, such a simple draping procedure has frequently proven unsatisfactory in that the drape became dislodged from its original position and exposed the patient to an increased degree of risk of contamination of the operative site. In such cases the extremity has been "draped free" or covered separately from the rest of the patient's body by a cotton stockinette drawn up to the distal end of the operative site. However, once either cotton or muslin is wet with blood or other liquids, its effectiveness as a bacterial barrier is greatly reduced.

With the advent of nonwoven fabrics, it became practical to produce surgical drapes of liquid-repellent material at a cost consistent with disposability. Thus, a variety of drape configurations has become available. Included among these are drapes designed specifically for covering patient extremities during surgery. In addition to overcoming the problem of reducing the bacterial barrier effectiveness through the use of liquid-repellent material, these drapes have been designed in a tubular construction and provided with adhesive attachment means so as to present a convenient, reliable, and quickly applied surgical drape for patient extremities.

Examples of patient extremity drapes of the type described may be found in the following U.S. Pats. Nos. 3,494,356 to Melges issued Feb. 10, 1970; 3,540,441 to Collins issued Nov. 17, 1970; 3,613,676 to Endres et al issued Oct. 19, 1971; 3,693,618 to Madden issued Sept. 26, 1972; 3,707,964 to Patience et al issued Jan. 2, 1973; 3,769,971 to Collins issued Nov. 6, 1973; and 3,777,749 to Collins issued Dec. 11, 1973.

While the disposable drapes described above and in the patents listed have important added benefits when compared with muslin sheets, they have not been entirely satisfactory. For example, it is desirable to provide such drapes with improved resistance to liquid penetration so that the tendency for liquids to strike through will be reduced. Further, nonwoven materials in use have demonstrated weakness in certain high stress areas particularly during surgery where movement of the covered extremity is required. In addition, even in cases where the material has been liquid-repellent, it has been desirous to prevent liquid from penetrating underneath the drape. Finally, it is always advantageous in terms of patient safety and utilization of hospital facilities to reduce the time required for preparing the patient, including draping.

The drape of the present invention provides a structure that satisfies these further requirements to a high degree while retaining the benefits associated with known disposable drapes for patient extremities.

SUMMARY

In accordance with the present invention a disposable drape for covering a patient limb or extremity during surgery is provided that is constructed from a laminate of a flexible nonwoven fabric providing a comfortable surface for contact with the patient and a flexible liquid barrier film for resistance to liquid strike-through. The drape of the invention is provided in a tubular form having a closed end and an opened end with a slit extending from the opened end partially along the length of the tube and having adhesive attachment means associated with the slit so that the drape can be fixed in place to reduce the risk of it being dislodged during the surgical procedure. The adhesive attachment also serves to isolate the operative site and prevent liquid from penetrating underneath the drape. In accordance with preferred embodiments of the invention the drape is formed by bonding a flat sheet of the film-nonwoven fabric laminate and reinforcing the bonded edges to provide increased protection against rupturing or tearing of the drape. Further improvements result from the selection of particular nonwoven materials and films as well as from the preferred method of telescope folding the drape which provides a compact package suitable for quickly covering the patient extremity and reducing the risk of contamination.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

Figure 1:
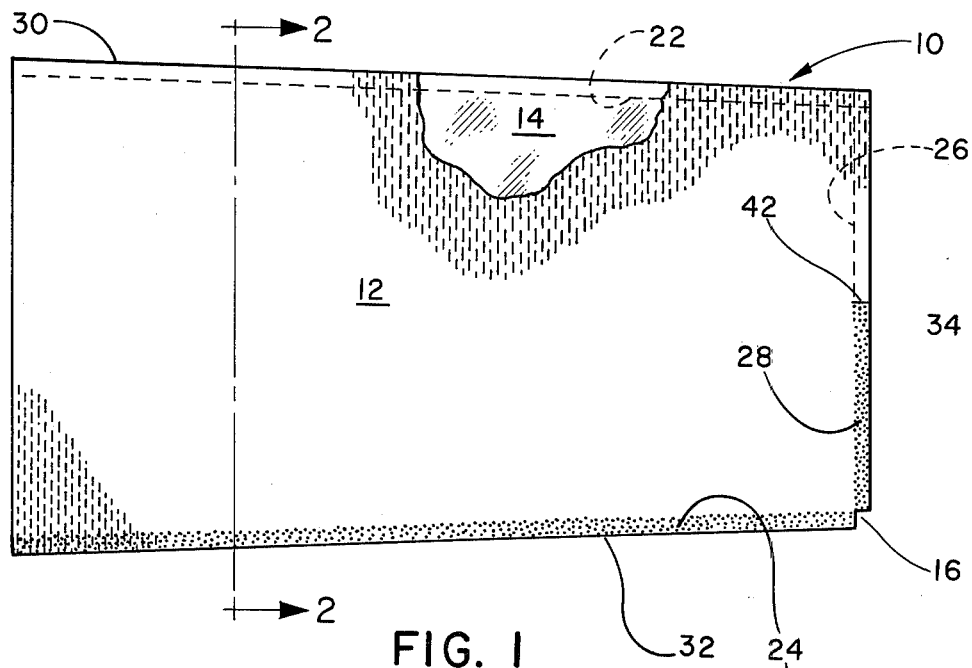
FIG. 1 illustrates a base sheet laminate suitable for forming a surgical drape in accordance with an embodiment of the present invention.
Figure 2:
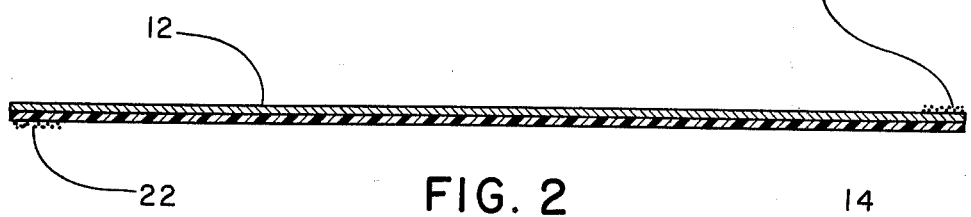
FIG. 2 is a cross-section of the drape of FIG. 1 taken along lines 2—2.

Turning to FIGS. 1 and 2, the embodiment illustrated therein will now be described in detail. As shown, prior to assembly, the drape of the invention includes a base sheet 10 which is formed by bonding a flexible nonwoven web 12 to a flexible plastic film 14. The film 14 and the nonwoven web 12 are preferably coextensive over at least a major portion of the base sheet area, and the overall shape of the base sheet is preferably slightly tapered. Corner 16 is preferably notched by removing a small square, and a small cut 42 is preferably made in end 34, both for each of assembly. Adhesive bonding strips 22, 24, 26 and 28 are provided for edge and end sealing of the drape. As illustrated, adhesive strips 22 and 26 are on the film surface while strips 24 and 28 are applied to the nonwoven web surface.

Figure 3:
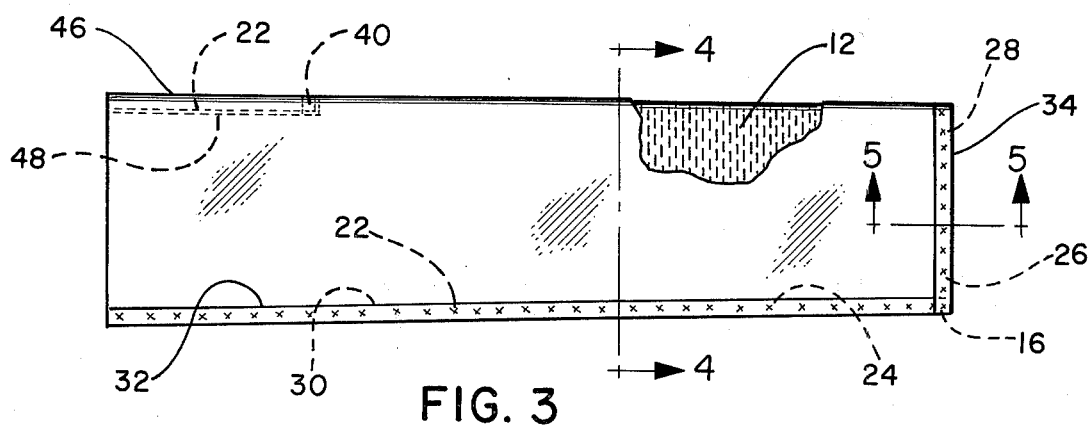
FIG. 3 is a drape in accordance with the present invention formed by folding the blank of FIG. 1 and bonding the edges and end.
Figure 4:
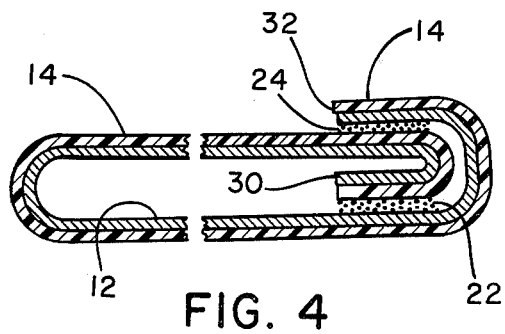
FIGS. 4 and 5 are cross-sections of the drape of FIG. 2 taken along lines 4—4 and 5—5.
Figure 5:
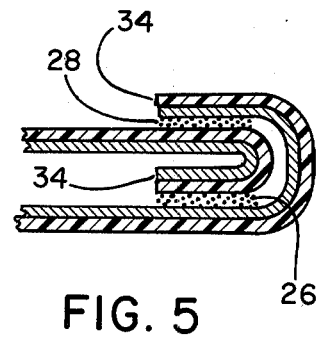

Turning to FIGS. 3–5, the construction of the formed drape of this embodiment will be further described. As shown, the base sheet 10 is folded so that the film is on the outside and the edges 30 and 32 can be bonded to form a seam. Preferably, this seam is double reinforced by folding edge 30 upon itself and overlapping that fold with edge 32 as illustrated in FIGS. 4 and 5 with the double adhesive layers 22 and 24 bonding the folds to form seams of increased strength. Similarly, end 34 is bonded by folding upon itself for half its length to cut 42 and overlapping that fold with the remaining half using adhesive strips 26 and 28 as shown in FIG. 5. In this manner, a strong and substantially liquid-proof drape is formed that is comfortable for the patient and has the increased security of reinforced seams. Opposite the seam formed by edges 30 and 32, a slit 46 is cut extending partially along the length of the drape as indicated to provide for a fenestration. As will be explained in greater detail in connection with subsequent Figures, adhesive strips 22 and 40 provide for attachment to the patient.

Figure 6:
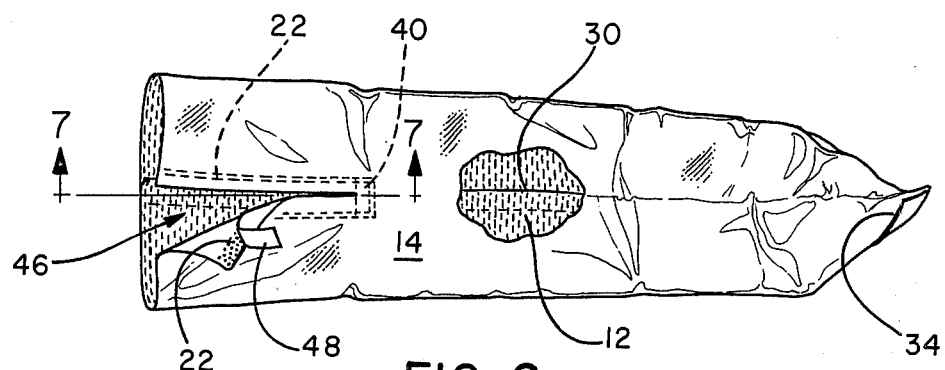
FIG. 6 illustrates a drape in accordance with the present invention unfolded prior to use.
Figure 7:
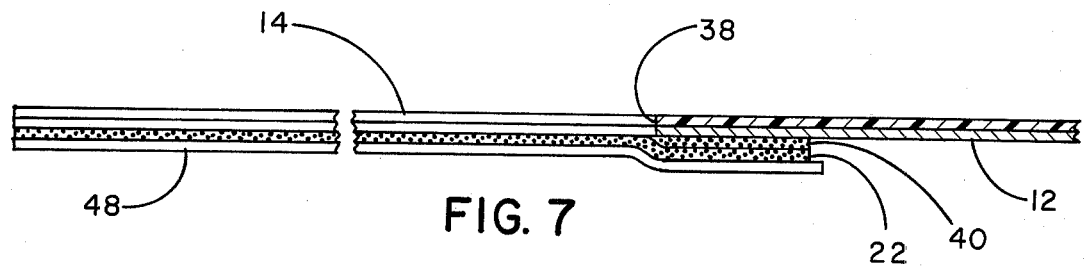
FIG. 7 is a section taken along lines 7—7 of FIG. 6.

Slit 46 is illustrated in FIGS. 6 and 7 having adjacent its edges adhesive layers 22 protected by release strip 48. The adhesive strips 22 preferably extend slightly beyond the end 38, and the end portion is covered by another transverse adhesive strip 40 to resist tearing of the drape. Adhesive strip 40 may be covered by the same release strip 48.

Figure 8:
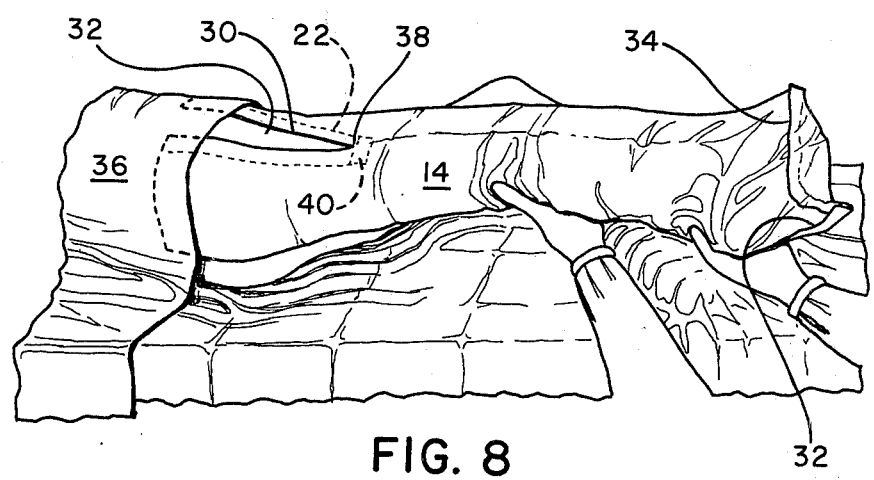
FIG. 8 shows the drape of FIG. 6 in use.

Considering now FIG. 8, the drape as previously illustrated will be described in use. Shown in a fragmentary view is a patient draped in preparation for hip surgery. The drape of the present invention is used to cover the patient's leg and is attached by means of the adhesive layers 22 to the patient's hip. In cooperation with the additional drape 36, the operative site is effectively sealed off and protected from the remaining parts of the patient. As shown, the split formed by edges 30 and 32 is reinforced at end 38 by means of an additional adhesive strip 40.

Figure 9:
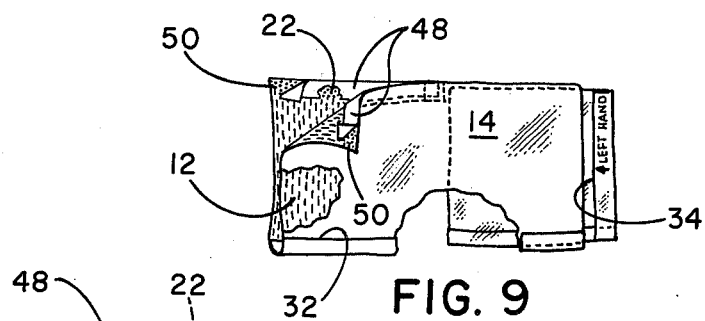
FIGS. 9–11 illustrate the preferred folding arrangement of the drape of the present invention.
Figure 10:
Figure 11:

Turning to FIGS. 9–11, the preferred folding arrangement for the drape of the present invention will be described. The fold preferably is in the same manner from both ends of the tubular drape construction and is initiated by telescoping a first fold inside the tube to about half the tube length. A second telescoping fold is made in a similar manner, and the folding may be repeated, if necessary, depending upon the length of the drape tube. When the tube has been telescoped from both ends to a desired length, release liner 48 is preferably folded back slightly on both adhesive strips 40 to expose portions 50 which are then pressed together to prevent premature unfolding. The drape is preferably then folded laterally as indicated in FIG. 11. Indicia as desired may be applied to indicate the type of drape and hand placement for unfolding. As illustrated the drape is then formed into a very compact structure which can be applied quickly with reduced contamination risk. Depending upon the desired application, it may be packaged individually or included as an element of a total draping system package.

EXAMPLE

A base material was formed by bonding a nonwoven layer to a plastic film. The nonwoven layer was a fabric formed by combining outer layers of cellulose wadding and inner layers of highly drafted fibers disposed angularly to each other. A spaced pattern of adhesive was disposed between each fiber layer and its adjacent wadding layer with the fibers in each fiber layer partially embedded in and held by the adhesive of its adjacent adhesive layer and partially embedded in and held by the adhesive in the other adhesive layer where it extends between the fibers of its adjacent fiber layer and with a portion of the adhesive in both adhesive layers joined where the adhesive patterns were superimposed. This material is described in more detail in Sokolowski et al U.S. Pat. No. 3,484,300 issued Dec. 16, 1969, assigned to the assignee of the present invention. The basis weight of the nonwoven fabric was 53g/yd. and it was treated for liquid repellency, conductivity, abrasion and lint resistance by a fluorocarbon bath. The film was a two mil antistatic polyethylene film manufactured by Clopay Film Corporation and it was coextensive with the nonwoven fabric.

The base material was cut into a basic configuration having a width at one end of about 31 inches and a width at the opposite end of about 27 inches. A one-half inch square was removed from one corner of the narrower end. A one inch adhesive strip layer was applied to the nonwoven web side of the base material adjacent one edge and continuing adjacent half the contiguous smaller end edge as illustrated in FIG. 1. A second similar adhesive strip was applied to the film side along the opposing edge and end portion, also as shown in FIG. 1.

The edges and the end of the base material were joined in a seam as illustrated in FIGS. 4 and 5 by overlapping folds and adhesive layers so that the tube was formed having a closed end and the film outside with the nonwoven material inside. The adhesive used for these bonding steps was an acrylic latex Jedbond 83-117, by Jed Company. A 14 inch slit was made oposite the seam and a 2 inch strip of 1 inch wide adhesive placed across the end of the slit. Two 15 inch adhesive strips 1 inch wide were placed adjacent each side of the slit and covering the end adhesive strip previously applied. The adhesive used was 3M Company 1522 tape with Poly-slik polyethylene coated paper release liners.

This formed tube was folded in the manner illustrated in FIGS. 9–11 by telescoping a first fold in 13 inches from each end and a second similar fold resulting in a total folded tube length of about 15 inches. The release strips were crimped and folded back slightly to expose adhesive portions of both strips which were pressed together to maintain the folded condition. This structure was then, itself, folded over by about 4 inches and stamped with indicia indicating the name of the drape and the preferred hand positioning. The drape was then ready for packaging, sterilization and use.

While a specific example of an adhesive has been given, any of the normally tacky and pressure-sensitive adhesives which are biologically acceptable may be used in the drape of the present invention. Adhesives of this class are generally composed of a film-forming elastomeric material, typically a natural or synthetic rubber, and some type of resin or other material to impart the desired degree of tack, wetting power, and specific adhesion. Typical resins include the rosin derivatives such as hydrogenated or dehydrogenated rosin in their esters. Various fillers, plasticizers, sterilizing agents, or other modifiers may also be used. For further description of such adhesives, see Kirk/Othmer "Encyclopedia of Chemical Technology", Second Edition, Volume I, Page 382 (Interscience 1963).

The release strip is preferably slightly larger than the adhesive areas being covered so as to provide a portion thereof which may be easily gripped for quick removal. This strip may be, illustratively, a plastic, heavy paper or nonwoven fabric having a release coating to which the adhesive only lightly adheres. Coatings suitable for these purposes include natural or synthetic waxes, metal salts or fatty acids, polymeric materials such as polyethylene or silicone polymers, for example. Release coatings are discussed in Kirk/Othmer's "Encyclopedia", Second Edition, Volume I, Page 1, et seq.

In addition to the specific film material of the example, other films may be used such as, antistatic polypropylene, for example "Extrel II" available from Extrudo Film Corporation, polyethylene methyl acrylate copolymer film manufactured by Edison Plastics Company, and polyvinyl chloride films. The film selected involves a matter of choice among those which provide a liquid-impervious barrier on the top surface of the drape so that liquids which are likely to contact this area cannot strike through the sheet. It also prevents the transfer of bacteria through the sheet to aid in insuring sterile conditions in the operative area. The film must be capable of remaining stable under the conditions encountered in the particular treatment to which the drape is subjected to render it sterile, for example, temperatures of about 270° F for steam sterilization or about 160° F for sterilization by means of ethylene oxide or the like.

In addition to the nonwoven fabric above described, other nonwoven fabrics may be utilized. For example, a scrim-reinforced tissue product available under the trademark KAYCEL from Kimberly-Clark Corporation may be utilized as well as random fiber reinforced tissue laminates.

Thus, it is apparent that there has been provided in accordance with the invention a surgical drape that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:
1. Surgical drape comprising a tube having an open end and a closed end and adapted to enclose a patient extremity characterized by,
    an inside surface of a flexible, strong, nonwoven material;
    at least a major portion of the outside surface of a flexible, liquid-proof film bonded to said nonwoven material;
    a slit extending from said open end partially along the length of said tube;
    adhesive attachment means on the inside of said tube and adjacent to both edges of said slit; and
    releasable portective covering for said adhesive attachment means.
2. The drape of claim 1 wherein the closed end of the slit is reinforced by crosslaid adhesive tape.
3. The drape of claim 1 further including overlapping, double reinforced side and end seams and wherein said slit is positioned opposite said side seam.
4. The drape of claim 1 wherein said nonwoven material is a cellulosic laminate.
5. The drape of claim 1 wherein said nonwoven material is a scrim reinforced material.
6. The drape of claim 1 wherein said liquid-proof film is polyethylene.
7. The drape of claim 1 telescope folded for improved speed and safety in application.

* * * * *

UNITED STATES PATENT AND TRADEMARK OFFICE
CERTIFICATE OF CORRECTION

PATENT NO. : 3,989,040

DATED : November 2, 1976

INVENTOR(S) : Lewis C. Lofgren et al.

It is certified that error appears in the above–identified patent and that said Letters Patent are hereby corrected as shown below:

Column 3, line 6, "each" should read -- ease --.

Column 4, line 45, "oposite" should read -- opposite --.

Column 6, line 27, "portective" should read -- protective --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks